United States Patent [19]

Horvath et al.

[11] 4,237,273

[45] Dec. 2, 1980

[54] BIS(NITROSOUREIDO)-POLYOL DERIVATIVES

[75] Inventors: Tibor Horváth; Endre Csányi; Sándor Eckhardt; Emilia Király neé Vida, all of Budapest, Hungary

[73] Assignee: Richter Gedeon Vegyeszeti Gyar RT, Budapest, Hungary

[21] Appl. No.: 925,822

[22] Filed: Jul. 17, 1978

[30] Foreign Application Priority Data

Dec. 29, 1977 [HU] Hungary .............................. GO 1386

[51] Int. Cl.³ .......................... A61K 31/70; C07H 5/06
[52] U.S. Cl. ......................................................536/53;
536/18; 424/180; 564/33; 564/60
[58] Field of Search ................. 536/53, 18; 260/553 R

[56] References Cited

U.S. PATENT DOCUMENTS

| | | | |
|---|---|---|---|
| 3,694,428 | 9/1972 | Hardegger et al. | 536/53 |
| 4,066,750 | 1/1978 | Smith et al. | 536/18 |
| 4,148,921 | 4/1979 | Suami | 260/553 R |
| 4,156,777 | 5/1979 | Kimura | 536/18 |
| 4,157,439 | 6/1979 | Suami | 536/18 |

FOREIGN PATENT DOCUMENTS 754895 7/1975 South Africa .............................. 536/18

*Primary Examiner*—Johnnie R. Brown
*Attorney, Agent, or Firm*—Young & Thompson

[57] ABSTRACT

The invention relates to bis(nitrosoureido)-polyol derivatives of general formula I $$B_1-A-B_2 \qquad (I)$$

wherein
A stands for an open chain polyol comprising 4 to 6 carbon atoms or a six-membered cyclic polyol, and
$B_1$ and $B_2$ being attached to two different carbon atoms of the chain A, are identical or different, and stand for a group of general formula II $$X-CH_2-CH_2-\underset{Y}{N}-CO-\underset{Z}{N}- \qquad (II)$$

wherein
X stands for a halogen atom and
Y and Z stand for a hydrogen atom or a nitroso group, with the restriction, that in $B_1$ and $B_2$ Y and Z must be different.

The above compounds possess valuable cytostatic activity.

18 Claims, No Drawings

BIS(NITROSOUREIDO)-POLYOL DERIVATIVES

The invention relates to new bis(nitrosoureido)-polyol derivatives.

More particularly, this invention relates to new bis(-nitrosoureido)-polyols having the general formula I $$B_1—A—B_2 \qquad (I)$$

wherein

A stands for an open-chain polyol, comprising 4 to 6 carbon atoms or a six-membered cyclic polyol, and $B_1$ and $B_2$, being attached to two different carbon atoms, preferably through 3 to 6 carbon atoms, of chain A, are identical or different, and stand for a group of the general formula II $$X—CH_2—CH_2—\underset{Y}{N}—CO—\underset{Z}{N}— \qquad (II)$$

wherein

X stands for a halogen atom and

Y and Z stand for a hydrogen atom or a nitroso group with the restriction, that in $B_1$ and $B_2$ Y and Z must be different.

The compounds of general formula I can be prepared according to the invention by nitrosation of a diureido compound of the general formula III

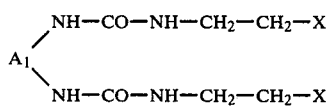

$$A_1 \begin{cases} NH—CO—NH—CH_2—CH_2—X \\ NH—CO—NH—CH_2—CH_2—X \end{cases} \qquad (III)$$

wherein X has the same meaning as above, and $A_1$ stands for an open chain polyol comprising 4 to 6 carbon atoms, or a six membered cyclic polyol, or an O-acetal derivative thereof, and the ureido groups are attached to two different carbon atoms of the chain of $A_1$, and, if desired, hydrolysing off the O-acetal group or groups by treatment with an acid.

In the compounds of general formula I A is preferably a di- or trideoxy-sugar alcohol of any configuration, that is a tetritol, pentitol, hexitol or cyclic hexitol derivative, such as erythritol, D,L-threitol, D-threitol, L-threitol, D-mannitol, galactitol, D-glucitol, D-iditol, L-iditol, D-arabitol, ribitol, xilitol, scylloinositol, D-inositol and mucoinositol derivative.

When in the compounds of general formula III $A_1$ is the O-acetal derivative of a polyol, then preferably O-isopropylidene or O-benzylidene derivatives are used.

The starting compounds of general formula III are new. They can be synthesized by known methods (T. P. Johnston at al., J. Med. Chem., 6, 669/1963/), by reacting the diamino derivatives of general formula IV $$H_2N—A_1—NH_2 \qquad (IV)$$

wherein $A_1$ has the same meaning as above, with 2-halogen-ethyl isocyanate or 3-(2-halogenethyl)-1-methyl-1-nitrosourea, or reacting the diisocyanate derivative of general formula V $$OC_3—A_1—NCO \qquad (V)$$

wherein $A_1$ has the same meaning as above, with 2-halogenethyl amine or ethylene imine, applying in the latter case a subsequent treatment with a haloid acid.

Nitrosation of compounds of general formula III can be carried out according to the literature [E. H. White, J. Am. Chem. Soc., 77, 6008 (1966); T. P. Johnston at al., J. Med. Chem., 9, 892 (1966)] in the presence of an organic or inorganic acid with an alkali nitrite, $N_2O_3$ or $N_2O_4$ or with nitrosyl chloride. In the reactions preferably dry organic acids, i.e. trifluoro acetic acid, formic acid, or acetic acid, is applied.

The obtained crude N-nitroso derivatives can be purified by recrystallization and/or column chromatography.

The compounds of general formula I possess more favourable cytostatic and toxic properties then the known representatives of compounds of this type, e.g. 1,3-bis(2-chloroethyl)-1-nitrosourea (BCNU) [T. P. Johnston at al., J. Med. Chem., 6, 669 (1963); 9, 892 (1966); V. DeVita et al., Cancer Res., 25, 1876 (1965); H. H. Hansen et al., Cancer Res. 31, 223 (1971)].

The biological activity of the compounds according to the invention on several experimental animal tumours are shown on the following compounds:

1. 1,4-bis[3-(2-chloroethyl)-N-nitrosoureido]-1,4-dideoxy-D,L-threitol
2. 1,6-bis[3-(3-chloroethyl)-N-nitrosoureido]-1,6-dideoxy-D-mannitol
3. 1,3-bis[3-(2-chloroethyl)-N-nitriosoureido]-1,2,3-trideoxyscylloinositol
4. 1-[3-(2-chloroethyl)-3-nitrosoureido]-4-[3-(2-chloroethyl)-1-nitrosoureido]-1,4-dideoxy-D,L-threitol
5. 1,4-bis[3-(2-chloroethyl)-3-nitrosoureido]-1,4-dideoxy-D,L-threitol
6. BCNU [1,3-bis(2-chloroethyl)-1-nitrosourea; reference compound].

I. Acute toxicity

Species: $BDF_1$ mice of both sexes

Treatment: a volume of 0.2 ml./10 g. body weight of a suspension of the tested compounds in water containing 2% of Tween-80 was used.

Number of animals: 10/dose

Number of doses: 6

Observation time: 21 days

The test results are shown in Table 1.

TABLE 1

| Compound number | $LD_{50}$ value, mg./kg. | |
|---|---|---|
| | i.p. | p.o. |
| 1 | 80 | 135 |
| 2 | 110 | 250 |
| 3 | 40 | 100 |
| 4 | 80 | 130 |
| 5 | 40 | 75 |
| 6 | 36 | 40 |

II. Antitumour activity

Transplantation:

The leukemia and ascites type tumours were transplanted intraperitoneally, using an amount of $10^5-10^7$ cells, while in the case of solid tumours, small pieces of tumours were implanted subcutaneously with a trocar.

Treatment:

Mice were treated with a volume of 0.1 ml./10 g. body-weight of a suspension of the tested compounds in water containing 2% of Tween-80, while rats were treated with a volume of 0.1 ml./100 g. bodyweight of a suspension of the tested compounds in water containing 5% of Tween-80.

Weight of the used animals:
mice: 20-23 g.
rats: 140-160 g.
Evaluation:

The ascites and leukemia-type tumours were evaluated with the exception of the Rausher leukemia by the increase of the life span and by complete recovery.

Life span increase (%) =

$$\frac{\text{life span of treated animals} \times 100}{\text{life span of untreated animals}} - 100$$

Recovery=90 days of tumour free life after transplantation.

In the case of solid tumours (Harding-Passey melanoma, S-180 and Yoshida sarcoma) the tumours were removed on the 8 to 14$^{th}$ day, and the inhibition was calculated by the weight of the tumours, using the following formula:

$$\text{Inhibition} = 100 - \frac{\text{weight of the treated tumour} \times 100}{\text{weight of control tumour}}$$

A similar method was applied in the case of the Rauscher leukemia too, but the weight of the spleen was taken, instead of the tumour, in the formula mentioned above.

TABLE 2

| Tumor | Compound number | Dose, mg./kg. from the 2nd day | | Increase in life span % | Recovery (90 day survival) |
|---|---|---|---|---|---|
| L-120 leukemia (strain: BDF$_1$ mice) | 1 | 7.5 | 1× i.p. | 45 | 2/8 |
| | | 15.0 | 1× i.p. | 29 | 3/8 |
| | | 30.0 | 1× i.p. | 230 | 7/8 |
| | | 12.5 | 1× p.o. | 23 | 1/8 |
| | | 25.0 | 1× p.o. | 111 | 3/8 |
| | | 50.0 | 1× p.o. | 84 | 4/8 |
| | | 12.5 | 3× p.o. | 30 | 3/8 |
| | | 25.0 | 3× p.o. | — | 6/8 |
| | 2 | 1.0 | 4× i.p. | 58 | 0/10 |
| | | 3.0 | 4× i.p. | 158 | 3/10 |
| | | 10.0 | 4× i.p. | 140 | 8/10 |
| | 3 | 15.0 | 1× i.p. | 180 | 5/8 |
| | | 10.0 | 4× p.o | 61 | 1/7 |
| | 6 | 3.0 | 4× i.p. | 40 | 0/8 |
| | | 10.0 | 4× i.p. | 405 | 6/7 |
| | | 24.0 | 1× p.o. | 48 | 0/8 |
| | | 10.0 | 4× p.o. | 106 | 1/8 |
| P-388 leukemia (strain: BDF$_1$mice) | 1 | 12.0 | 4× i.p | — | 7/8 |
| | 2 | 10.0 | 4× i.p. | 131 | 0/8 |
| | 3 | 3.0 | 4× i.p. | 101 | 0/8 |
| | 6 | 3.0 | 4× i.p. | 51 | 0/8 |
| NK/Ly ascites lymphoma (strain: CFLP mice) | 1 | 1.5 | 4× i.p. | 433 | 6/8 |
| | | 3.0 | 4× i.p. | — | 8/8 |
| | | 30.0 | 4× p.o. | 89 | 1/7 |
| | 2 | 0.3 | 4× i.p. | — | 6/7 |
| | 3 | 0.1 | 4× | — | 7/7 |
| | | 10.0 | 4× p.o. | 61 | 1/7 |
| | 6 | 0.3 | 4× i.p. | — | 0/7 |
| | | 1.0 | 4× i.p. | — | 5/7 |
| | | 3.0 | 4× i.p. | — | 7/7 |
| Ehrlich acites carcinoma (strain: CFLP mice) | 1 | 1.5 | 4× i.p. | — | 6/8 |
| | 2 | 1.0 | 5× i.p. | 96 | 4/7 |
| | 3 | 1.0 | 5× i.p. | 46 | 2/7 |
| | 6 | 3.0 | 5× i.p. | 60 | 1/6 |

TABLE 3

| Tumour | Compound number | Dose, mg./kg. from the 2nd day | | Inhibition % | |
|---|---|---|---|---|---|
| Rausher leukemia (strain CFLP mice) | 1 | 10.0 | 6× i.p. | 78 | |
| | 2 | 10.0 | 4× i.p. | 86 | Number of animals: 10/dose |
| | 3 | 10.0 | 6× i.p. | 100 | |
| | 4 | 10.0 | 4× i.p. | 100 | |
| | | 10.0 | 4× p.o. | 100 | |
| | 5 | 3.0 | 4× i.p. | 75 | |
| | | 10.0 | 4× p.o. | 100 | |
| | 6 | 10.0 | 6× i.p. | 97 | |
| Harding-Passey melanoma (strain CFLP mice) treatment: from the 4$^{th}$ day after transplantation | 1 | 24.0 | 1× i.p. | 81 | |
| | | 10.0 | 5× p.o. | 96 | |
| | 2 | 10.0 | 9× i.p. | 42 | Number of animals 10/dose |
| | | 10.0 | 9× p.o. | 59 | |
| | 3 | 3.0 | 9× i.p. | 54 | |
| | | 10.0 | 9× p.o. | 38 | |
| | 6 | 3.0 | 9× i.p. | 64 | |
| | | 3.0 | 9× p.o. | 71 | |
| S-180 s.c. sarcoma (strain: CFLP mice) | 1 | 3.0 | 2× i.p. | 43 | |
| | | 12.0 | 4× i.p. | 80 | |
| | | 10.0 | 4× p.o. | 42 | Number of animals: 8/dose |
| | 2 | 10.0 | 5× i.p. | 56 | |
| | | 30.0 | 5× p.o. | 51 | |
| | 6 | 10.0 | 5× i.p. | 65 | |
| | | 10.0 | 5× p.o. | 32 | |
| Yoshida s.c. sarcoma (strain: CFY rats) | 1 | 24 | 1× i.p. | 76 | |
| | | 12 | 4× i.p. | 99 | |
| | 2 | 10 | 4× i.p. | 84 | Number of animals: 7/dose |
| | | 30 | 4× p.o. | 75 | |
| | 3 | 10 | 4× i.p. | 86 | |
| | 4 | 10 | 4× i.p. | 82 | |
| | | 3 | 4× p.o. | 50 | |
| | 5 | 10 | 2× p.o. | 99 | |
| | | 3 | 4× p.o. | 62 | |
| | 6 | 10 | 4× i.p. | 95 | |
| | | 10 | 4× p.o. | 100 | |
| | | 3 | 4× p.o. | 45 | |

TABLE 4

| Tumour | Compound number | Dose mg./kg. on 6th day | | Recovery (90 day survival) |
|---|---|---|---|---|
| Developed Yoshida s.c. sarcoma | 1 | 50 | 1× i.p. | 5/7 |
| | 2 | 30 | 1× i.p. | 4/7 |
| | 6 | 30 | 1× i.p. | 0/7 |

III. Experiments for establishing the way and duration of activity

Mice, being infected with Ehrlich ascites carcinoma, were treated intraperitoneally on the 6$^{th}$ day after transplantation with equitoxic doses of compounds 1, 2 and 6. The duration of the activity was investigated by determining the total cell number and the way of action by determining the mitosis index* and the thymidine index**. It could be shown that both compounds 1 and 2 inhibit the increase of the total cell number for 35 days, while a similar inhibition of the reference compound 6 lasts only for 17 days. As far as the quality of the activity is concerned, compounds 1 and 2 decrease the mitosis-index and the thymidine index in 24 hours by 90%, while in the case of compound 6 the decrease amounts only to 45 to 50%, and the maximum is reached on the 4$^{th}$ day.

*mitosis index=number of dividing cells/1000 tumour cells
**thymidine index=³H-thymidine incorporation into the DNS of the tumour cell.

IV. Summary of the results of the biological investigation:

1. The activity of the compounds of general formula I is on most tumour tests more favourable, in some cases (i.e. Ehrlich ascites carcinoma, P-388 leukemia) even by an order of magnitude, than that of the reference compound BCNU.

2. The compounds are very active on L-1210 leukemia, even on oral application, while BCNU has only an unsignificant oral activity.

3. The very malignant Yoshida subcutaneous sarcoma, which kills the animals in 7–8 days, was cured in high percent by the claimed compounds, administered as a single dose on the 6$^{th}$ day, while BCNU proved to be inactive in this system.

4. The action of a single dose lasts much longer in case of the novel compounds, compared to BCNU.

5. The activity on the mitosis and the DNS synthesis differs qualitatively from that of BCNU; it develops more rapidly and is much stronger then in case of BCNU.

6. The oral and acute toxicities of the novel compounds and more favourable than those of BCNU.

The compounds of general formula I can be applied both orally and parenterally, especially as intravenous injections.

For oral application tablets, capsules, suspensions, syrups and other forms can be used, for parenteral application a physiologically acceptable solvent can be used.

The daily dose of the compounds amounts to 20 to 200 mg. for adults. The applied dose depends naturally from the state of progress of the disease, from the body weight, age, general state of health of the patient as well as from other factors, which have to be taken into consideration during the treatment, such as the toxicity and the side effects.

The process for producing compounds according to the invention is further illustrated by means of the following Examples.

EXAMPLE 1

Preparation of 1,4-bis[3-(2-chloroethyl)-N-nitrosoureido]-1,4-dideoxy-D,L-threitol To a stirred solution of 1,4-bis[3-(2-chloroethyl)ureido]-1,4-dideoxy-D,L-threitol in dry trifluoro acetic acid (16.55 g., 0.2 moles) pulverized sodium nitrite (13.8 g., 0.2 moles) is added in small portions during 2 hours at 0° to 4° C. The reaction mixture is stirred for 3 hours at 0° to 4° C., then ice-water (1200 ml.) is added and stirring is continued for 1 hour. The separated crystals are filtered, washed with water and ether, and dried over phosphorus pentoxide under reduced pressure. Yield: 9.2 g.; m.p.: 117°–119° C. (decomp.). From the mother liquor further 4.4 g. crystalline product separates on cooling overnight.

Thin layer chromatography (t.l.c.) is performed on Kieselgel 60 HF$_{254+366}$ (Reanal, Budapest) covered plates, using dichloromethane and isopropanol (9.5:0.5) as eluent; R$_f$=0.30, 0.37 and 0.43. The crude N-nitroso derivative is suspended in dichloromethane, filtered, washed and then recrystallized from a mixture of tetrahydrofurane and dichloromethane and ethyl acetate to give pure 1-[3-(2-chloroethyl)-1-nitrosoureido]-4-[3-(2-chloroethyl)-3-nitrosoureido]-1,4-dideoxy-D,L-threitol; m.p.: 136°–136.5° C. (decomp.); R$_f$=0.37.

The above filtrate is combined with the mother liquors of the recrystallization and is evaporated at room temperature at reduced pressure. The solid residue containing the isomers is separated by column chromatography to give 1,4-bis[3-(2-chloroethyl)-3-nitrosoureido]- [m.p.: 96°–97° C. (decomp.), R$_f$=0.3] and 1,4-bis[3-(chloroethyl)-1-nitrosoureido]-1,4-dideoxy-D,L-threitol [m.p.: 115°–116° C. (decomp.); R$_f$=0.43].

The analytical data of both the mixture of the isomers and the separated isomers are in agreement with the calculated values.

1,4-Bis[3-(2-chloroethyl)-ureido]-1,4-dideoxy-D,L-threitol, used as starting material, is prepared as follows:

To a vigorously stirred solution of 6.0 g (0.05 moles) of 1,4-diamino-1,4-dideoxy-D,L-threitol (H. R. Meyer at al., Helv. Chim. Acta 46, 2685/1963/) in water (70 ml.) 2-chloroethyl isocyanate (11.0 g., 0.105 moles) is added dropwise. After 3.5 hours stirring the cooled reaction mixture is filtered and the white crystalline product is washed with water, ethanol and ether. Yield: 14.9 g.; m.p.: 149°–150° C.; R$_f$=0.52 (mixture of ethyl acetate, water and acetic acid in a ratio of 15:2:2).

EXAMPLE 2

Preparation of 1,4-bis[3-(2-chloroethyl)-N-nitrosoureido]-1,4-dideoxy-erythritol Method A To a stirred solution of 1,4-bis[3-(2-chloroethyl)ureido]-1,4-dideoxy-erythritol (6.62 g., 0.02 moles) in 99 to 100% formic acid (80 ml.) sodium nitrite (4.14 g., 0.06 moles) is added in portions during 2 hours at 0° to 4° C. The reaction mixture is stirred with cooling for 3 hours, then ice-water (200 ml.) is added, and the product is extracted with dichloromethane. The organic solution is washed neutral with an aqueous suspension of sodium hydrogen carbonate, then it is dried on sodium sulfate and evaporated under reduced pressure. The dry residue is several times triturated with ether, and the combined extracts are concentrated under reduced pressure. On cooling pale yellow crystals deposit which are filtered, washed with ether and dried over phosphorus pentoxide. Yield: 0.78 g.; m.p.: 117°–118° C. (decomp.).

The product can be recrystallized from ethyl acetate or ethanol; m.p.: about 122° C. (decomp.).

Analysis for C$_{10}$H$_{18}$N$_6$O$_6$Cl$_2$ (389.22): Calculated: C 30.86; H 4.63; N 21.60; Cl 18.22; Found: C 31.20; H 4.82; N 21.38; Cl 18.11.

1,4-Bis[3-(2-chloroethyl)-ureido]-1,4-dideoxyerythritol, used as starting material, is prepared as follows:

To a vigorously stirred solution of 1,4-diamino-1,4-dideoxy-erythritol (36.0 g., 0.3 moles) (H. R. Meyer at al., Helv. Chim. Acta., 46, 2685/1943/) in water (360 ml.) 2-chloroethyl-isocyanate (65.4 g., 0.62 moles) is added gradually at 0°–2° C. The crystalline product which precipitates is filtered after 4 hours of stirring and cooling, and is washed with water, ethanol and ether. Yield: 96 g.; m.p.: 175°–176° C. The product is dissolved in cc. hydrochloric acid to give after filtration and dilution with ice-water a crystalline product. Yield: 83.2 g.; m.p.: 177°–178° C. R$_f$=0.6 (mixture of ethyl acetate, water and acetic acid in a ratio of 15:2:2).

Method B

To a stirred solution of 1,4-bis[3-(2-chloroethyl)ureido]-1,4-dideoxy-erythritol (6.60 g., 0.02 moles) in dry trifluoro acetic acid (63 ml.) sodium nitrite (8.22 g., 0.12 moles) is added during 1.5 hours at 0° to 2° C. After stirring for 4 hours the reaction mixture is diluted with ice-water (350 ml.) and the precipitate is extracted with dichloromethane. The organic solution is processed according to method A to give a crude product (1.58 g.); m.p.: 116°–118° C. (decomp.). The mother liquor is evaporated and the dry residue is dissolved at 0° C. in trifluoro acetic acid (40 ml.) to give after dilution with water and processing as described above a further crop of 1.2 g. Repetition of this treatment affords a third crop of 0.84 g. The combined material is recrystallized from ethyl acetate or ethanol to give a product identical with that obtained via method A.

Method C

A stream of $N_2O_3$ is led into a solution of 1,4-bis-[3-(2-chloroethyl)-ureido]-1,4-dideoxy-erythritol (6.60 g., 0.02 moles) in cc. hydrochloric acid (50 ml.) for 3 hours at 0°–4° C. The reaction mixture is then diluted with ice-water (150 ml.) and extracted with chloroform. The organic solution is washed neutral with an aqueous suspension of sodium hydrogen carbonate, dried and evaporated. The residue is dissolved in ethyl acetate and chilled overnight. The yellow crystals are filtered and washed with water and ether. Yield: 0.78 g.; m.p.: 118°–119° C. (decomp.). The mother liquor is evaporated and the residue gives on treatment with formic acid at 0° C. according to Example 3 a further crop of 0.74 g. The crude product is recrystallized from ethyl acetate to give a material identical with that obtained via method A.

Method D

To a solution of 1,4-bis[3-(2-chloroethyl)-ureido]-1,4-dideoxy-2,3-O-isopropylidene-erythritol (0.74 g., 0.002 moles) in 99–100% formic acid (5 ml.) sodium nitrite (0.89 g., 0.012 moles) is given during 2 hours at 0°–4° C. The reaction mixture is diluted after 3 hours of stirring and cooling with water (5 ml.). After 1 hour cooling the mixture is further diluted with water (25 ml.) and extracted with chloroform. The organic solution is washed neutral with a sodium hydrogen carbonate, dried over sodium sulfate and evaporated. The residue is separated by column chromatography on Kieselgel-40 (Reanal, Budapest) using a mixture of chloroform and methanol of a ratio of 9:1 for elution. Evaporation of the fractions with $R_f=0.58$ gives 0.29 g. material identical with that obtained via method A (m.p.: 122° C./decomp./).

1,4-Bis[3-(2-chloroethyl)-ureido]-1,4-dideoxy-2,3-O-isopropylidene-erythritol, used as starting material, can be obtained as follows:

Step a:

Preparation of 1,4-diazido-1,4-dideoxy-erythritol

A solution of 1,2:3,4-dianhydro-erythritol (17.2 g., 0.2 moles) (P. W. Feit, Chem. Ber., 93, 116/1960/) in 95% aqueous methyl cellosolve (200 ml.) is treated with sodium azide (52.0 g., 0.8 moles) and ammonium chloride (10.6 g., 0.2 moles) and stirred for 1 hour at 90° C. and then for 1 hour at the boiling point.

The cooled reaction mixture is diluted with acetone (200 ml.). The salts precipitated are filtered off, and the filtrate is evaporated at diminished pressure. The residue is again treated with acetone for removing the salts. The residue of the evaporated filtrate is extracted with hot benzene (240 ml.). From the decanted solution crystalline material separates on cooling. Yield: 24.8 g.; m.p.: 89°–90° C.; $R_f=0.62$ (mixture of ethyl acetate and chloroform in a ratio of 8:2).

Step b:

Preparation of 1,4-diazido-1,4-dideoxy-2,3-O-isopropylidene-erythritol

The diazide obtained according to step a (20.1 g., 0.118 moles) is dissolved in dry acetone (460 ml.) containing 100% sulfuric acid (16 ml.). The reaction mixture is kept at room temperature for 3 hours and then it is made neutral by stirring (5 hours) with sodium carbonate (100 g.). The filtered solution is evaporated and acetone is removed by reevaporation of the residue with benzene. The semi-solid residue is filtered with hexane, and thus crystals (0.5 g.) of the unchanged starting material are obtained. The filtrate is evaporated, the residue is dissolved in chloroform and washed with water. After drying on sodium sulfate the solvent is removed by evaporation under diminished pressure to give an oily product. Yield: 16.7 g.; $R_f=0.75$ (on Kieselgel G, in a mixture of ethyl acetate and chloroform in a ratio of 8:2).

Step c:

Preparation of 1,4-diamino-1,4-dideoxy-2,3-O-isopropylidene-erythritol

A solution of the product obtained in step b (20.7 g., 0.091 moles) in ether (125 ml.) is given to a solution of LiAlH$_4$ (22.5 g.) in tetrahydrofurane (450 ml.). The reaction mixture is boiled for 4 hours, cooled and treated with a solution of potassium sodium tartrate (22.0 g.) in water (45 ml.). After 30 minutes of stirring the precipitate is filtered off and washed with tetrahydrofurane. The filtrate is dried on sodium sulfate, evaporated under nitrogen at diminished pressure and reevaporated with benzene. The residue is distilled at diminished pressure. Yield: 11.9 g.; b.p.: 79°–81° C./0.4 mmHg; dipicrate m.p.: 222° C. (decomp.); dihydrochloride m.p.: 310° C. (decomp.). $R_f=0.58$ (on Kieselgel G, in a 3:5:2:0.5 mixture of chloroform, methanol, 2 M ammonium hydroxide and acetic acid).

Step d:

Preparation of 1,4-bis[3-(2-chloroethyl)-ureido]-1,4-dideoxy-2,3-O-isopropylidene-erythritol To a solution of the diamine obtained in step c (5.6 g., 0.035 moles) in ether (80 ml.) 2-chloroethyl-isocyanate (7.75 g., 0.070 moles) is added. The precipitated crystalline compound is filtered off after 3 hours at 20° C. The crude product (12.15 g.) is dissolved in acetone, freed from a small amount of unsolved material by filtration and crystallized; m.p.: 143.5°–144.5° C.; $R_f=0.81$ (Kieselgel G, in a 1:1 mixture of acetone and isopropanol).

EXAMPLE 3

Preparation of 1,6-bis[3-(2-chloroethyl)-N-nitrosoureido]-1,6-dideoxy-D-mannitol To a stirred solution of 1,6-bis[3-(2-chloroethyl)ureido]-1,6-dideoxy-D-mannitol (3.91 g., 0.01 moles) in 99–100% formic acid (45 ml.) sodium nitrite (5.52 g., 0.08 moles) is added during 2 hours at 0° to 2° C. The reaction mixture is stirred with cooling for 4 hours and after dilution with ice-water (220 ml.) for another hour, it is extracted with dichloromethane (5×40 ml.) and subsequently with ethyl acetate (3×80 ml.). The combined ethyl acetate extracts are washed with water, then with a solution of sodium hydrogen carbonate, dried on sodium sulfate and concentrated at diminished pressure. The crystals which deposit on cooling are filtered.

Yield: 2.1 g.; m.p.: 103°-104° C. The residue obtained after evaporation of the filtrate is extracted with dichloromethane, and the residue is crystallized from ether to give a second crop of 0.56 g. The combined materials are recrystallized from ethyl acetate or isopropanol; m.p.: 108°-109° C. (decomp.); $[\alpha]_D^{20} = +17.8°$ (c=1, in ethyl acetate).

Analysis for $C_{12}H_{22}N_6O_8Cl_2$ (449.23): Calculated: C 32.08; H 4.93; N 18.76; Cl 15.79; Found: C 32.27; H 4.99; N 18.66; Cl 15.59.

1,6-Bis-[3-(2-chloroethyl)-ureido]-1,6-dideoxy-D-mannitol, used as starting material, can be prepared as described below:

To a vigorously stirred solution of 1,6-diamino-1,6-dideoxy-D-mannitol (6.7 g., 0.037 moles) (W. N. Haworth at al., J. Chem. Soc., 1944, 155) in water (74 ml.) 2-chloroethyl isocyanate (8.28 g., 0.078 moles) is added below 4° C. The formed crystalline material is filtered off after 3.5 hours and is washed with water, ethanol and ether. Yield: 13.7 g.; m.p.: 175°-176° C. (decomp.). After recrystallization from acetic acid-water, m.p.: 177°-177.5° C.; $[\alpha]_D^{20} = -2.93°$ (c=1, in dimethyl formamide); $R_f = 0.35$ (on Kieselgel G, in a 15:2:2 mixture of ethyl acetate, water and acetic acid).

EXAMPLE 4

Preparation of
1,6-bis[3-(2-chloroethtyl)-N-nitrosoureido]-1,6-dideoxy galactitol To a stirred solution of 1,6-bis[3-(2-chloroethyl)ureido]-1,6-dideoxy galactitol (2.34 g, 0.06 moles) in dry trifluoro acetic acid (20 ml.) sodium nitrite (2.07 g., 0.03 moles) is added during 2 hours at 0°-2° C. The reaction mixture is diluted after 3.5 hours with ice-water (120 ml.), the precipitated crystals are filtered after further 2 hours of cooling and are washed with water, acetone and ether. Yield: 2.31 g.; m.p.: 140°-143° C. (decomp.). After recrystallization from ethanol or ethyl acetate, m.p.: 146°-148° C. (decomp.).

Analysis: for $C_{12}H_{22}N_6O_8Cl_2$ (449.23): Calculated: C 32.08; H 4.93; N 18.71; Cl 15.79; Found: C 31.92; H 4.97; N 18.66; Cl 15.62.

1,6-Bis[3-(2-chloroethyl)-ureido]-1,6-dideoxy galactitol, used as starting material, can be prepared as follows:

Step a:
Preparation of 1,6-bis[3-(2-chloroethyl)-ureido]-1,6-dideoxy-2,3:4,5-di-O-isopropylidene galactitol To a stirred solution of 1,6-diamino-1,6-dideoxy-2,3:4,5-di-O-isopropylidene galactitol (13.0 g., 0.05 moles) [J. W. W. Morgan et al., J. Am. Chem. Soc., 78, 2496 (1956)] in water (130 ml.) 2-chloroethyl isocyanate (10.8 g., 0.103 moles) is added at 0° to 2° C. The precipitated crystalline product is filtered after 3.5 hours of cooling and washed with water and ether. Yield: 21.3 g.; m.p.: 147°-148° C. After recrystallization from acetone m.p.: 185°-186° C. (decomp.); $R_f = 0.72$ (on Kieselgel G, in a 1:1 mixture of isopropanol and acetone).

Step b:
Preparation of 1,6-bis[3-(2-chloroethyl)-ureido]-1,6-dideoxy galactitol

A solution of the compound described in step a (7.4 g., 0.0157 moles) in 85% aqueous trifluoro acetic acid (25 ml.) is kept overnight at room temperature and then diluted with water (360 ml.). The precipitated crystalline compound is filtered after cooling and washed with water, ethanol and ether. Yield: 5.7 g.; m.p.: 190°-191.5° C. (decomp.); $R_f = 0.62$ (on Kieselgel G, in a mixture of acetone and isopropanol of a ratio of 1:1).

EXAMPLE 5

Preparation of
1,3-bis[3-(2-chloroethyl)-3-nitrosoureido]-1,2,3-trideoxy-scylloinositol Method A To a stirred solution of 1,3-bis[3-(2-chloroethyl)ureido]-1,2,3-trideoxy-scylloinositol (1.86 g., 0.005 moles) in trifluoro acetic acid (14 ml.) sodium nitrite (1.7 g., 0.025 moles) is added during 2 hours at 0°-2° C. After 4 hours the reaction mixture is diluted with ice-water (140 ml.) and after further one hour the precipitated crystals are filtered and then washed with water and ether. Yield: 1.98 g.; m.p.: 118°-120° C. After recrystallization from ethanol, m.p.: about 126°-127° C. (decomp.).

Analysis for $C_{12}H_{20}N_6O_7Cl_2$ (431.24): Calculated: C 33.42; H 4.67; N 19.48; Cl 16.44; Found: C 33.44; H 4.81; N 19.14; Cl 16.31.

Method B

A stream of $N_2O_3$ is passed through a stirred solution of 1,3-bis[3-(2-chloroethyl)-ureido]-1,2,3-trideoxy-scylloinositol (2.2 g., 0.006 moles) in conc. hydrochloric acid (20 ml.) for 4 hours. The reaction mixture is diluted gradually with ice-water (70 ml.) and the precipitated crystals are filtered and washed with water and ether. Yield: 2.3 g. The compound is identical with that obtained via method A.

1,3-Bis[3-(2-chloroethyl)-ureido]-1,2,3-trideoxy-scylloinositol used as starting material can be prepared as follows:

To a vigorously stirred solution of 1,3-diamino-1,2,3-trideoxy-scylloinositol (5.9 g., 0.036 moles) (M. Nakasima at al., Liebigs Ann. Chem. 689, 235/1966/; H. E. Carter at al., J. Am. Chem. Soc., 83, 3723/1961/) in water (150 ml.) 2-chloroethyl isocyanate (7.9 g., 0.075 moles) is added at 0°-2° C. The formed crystalline precipitate is filtered off after 3.5 hours and washed with water, ethanol and ether. Yield: 11.7 g.; m.p.: 194°-196° C. After recrystallization from a mixture of formic acid and water m.p.: 201°-203° C. (decomp.); $R_f = 0.25$ (on Kiselgel G, in a mixture of ethyl acetate, water and ethanol of a 15:2:2 ratio).

EXAMPLE 6

Preparation of
1,3-bis[3-(2-chloroethyl)-3-nitrosoureido]-1,3-dideoxy-scylloinositol To a vigorously stirred solution of 1,3-bis[3-(2-chloroethyl)-ureido]-1,3-dideoxy-scylloinositol (3.89 g., 0.01 moles) in dry trifluoro acetic acid sodium nitrite (64.8 g., 0.07 moles) is added during 2 hours at 0°-2° C. After 3 hours the reaction mixture is diluted gradually with ice-water (400 ml.), and after further one hour of stirring the deposited crystals are filtered and are washed with water, ethanol and ether. Yield: 4.35 g.; m.p.: 137°-142° C. (decomp.). The crude product is purified by column chromatography on Kieselgel-40, using a 8:2 mixture of acetone and ether for elution. The fractions having $R_f = 0.7$ are combined, evaporated (3.5 g.) and the residue is recrystallized from acetone; m.p.: 146°-150° C. (decomp.).

Analysis for $C_{12}H_{20}N_6O_8Cl_2$ (447.24): Calculated: C 32.32; H 4.51; N 18.79; Cl 15.85; Found: C 32.37; H 4.55; N 18.65; Cl 15.79.

1,3-Bis[3-(2-chloroethtyl)-ureido]-1,3-dideoxy-scyl-loinositol used as starting material can be prepared as follows:

To a vigorously stirred solution of 1,3-diamino-1,3-dideoxy-scylloinositol. 0.5 H₂O (4.6 g., 0.025 moles) (R. L. Peck et al., J. Am. Chem. Soc., 68, 776/1946/) in water (55 ml.) 2-chloroethyl isocyanate (5.79 g., 0.055 moles) is added at 0°–2° C. After 3.5 hours the precipitated crystals are filtered and washed with water, ethanol and ether. Yield: 6.15 g.; m.p.: 189°–190° C. (decomp.); $R_f$=0.33 (on Kiselgel G, in a 15:4:4 mixture of ethyl acetate, water and acetic acid.

EXAMPLE 7

Oral tablets, containing 25 mg. of active ingredient and having the following composition are prepared:

| | |
|---|---|
| 1,4-bis[3-(2-chloroethyl)-N-nitrosoureido]-1,4-dideoxy-D,L-threitol | 25 mg. |
| Corn-starch | 70 mg. |
| Lactose | 20 mg. |
| Polyvinylpyrrolidone | 2 mg. |
| Talcum | 2 mg. |
| Colloidal silicium dioxide | 0.5 mg. |
| Magnesium stearate | 0.5 mg. |

The average weight of one tablet amounts to 120 mg. The tablets are covered by a film coat.

What we claim is:
 1. 1,4-Bis[3-(2-chloroethyl)-N-nitrosoureido]-1,4-dideoxy-D,L-threitol.
 2. 1-[3-(2-Chloroethyl)-3-nitrosoureido]-4-[3-(2-chloroethyl)-1-nitrosoureido]-1,4-dideoxy-D,L-threitol.
 3. 1,4-Bis[3-(2-chloroethyl)-1-nitrosoureido]-1,4-dideoxy-D,L-threitol.
 4. 1,4-Bis[3-(2-chloroethyl)-3-nitrosoureido]-1,4-dideoxy-D,L-threitol.
 5. 1,4-Bis[3-(2-chloroethyl)-N-nitrosoureido]-1,4-dideoxy-erythritol.
 6. 1-[3-(2-Chloroethyl)-3-nitrosoureido]-4-[3-(2-chloroethyl)-1-nitrosoureido]-1,4-dideoxy-erythritol.
 7. 1,4-Bis[3-(2-chloroethyl)-1-nitrosoureido]-1,4-dideoxy-erythritol.
 8. 1,4-Bis[3-(2-chloroethyl)-3-nitrosoureido]-1,4-dideoxy-erythritol.
 9. 1,6-Bis[3-(2-chloroethyl)-N-nitrosoureido]-1,6-dideoxy-D-mannitol.
 10. 1-[3-(2-Chloroethyl)-3-nitrosoureido]-6-[3-(2-chloroethyl)-1-nitrosoureido]-1,6-dideoxy-D-mannitol.
 11. 1,6-Bis[3-(2-chloroethyl)-1-nitrosoureido]-1,6-dideoxy-D-mannitol.
 12. 1,6-Bis[3-(2-chloroethyl)-3-nitrosoureido]-1,6-dideoxy-D-mannitol.
 13. 1,3-Bis[3-(2-chloroethyl)-3-nitrosoureido]-1,2,3-trideoxy-scylloinositol.
 14. 1,3-Bis[3-(2-chloroethyl)-3-nitrosoureido]-1,3-dideoxy-scylloinositol.
 15. 1,6-Bis[3-(2-chloroethyl)-N-nitrosoureido]-1,6-dideoxy-galactitol.
 16. 1-[3-(2-Chloroethyl)-3-nitrosoureido]-6-[3-(2-chloroethyl)-1-nitrosoureido]-1,6-dideoxy-galactitol.
 17. 1,6-Bis[3-(2-chloroethyl)-1-nitrosoureido]-1,6-dideoxy-galactitol.
 18. 1,6-Bis[3-(2-chloroethyl)-3-nitrosoureido]-1,6-dideoxy-galactitol.

* * * * *